United States Patent [19]

Oja et al.

[11] 4,364,676
[45] Dec. 21, 1982

[54] HEAT TRANSFER METER

[75] Inventors: Viktor Oja; Sigvard Wikström, both of Skellefteå, Sweden

[73] Assignee: Memoteknik AB, Skellefteå, Sweden

[21] Appl. No.: 217,113

[22] PCT Filed: Mar. 13, 1980

[86] PCT No.: PCT/SE80/00077
   § 371 Date: Nov. 13, 1980
   § 102(e) Date: Nov. 13, 1980

[87] PCT Pub. No.: WO80/01954
   PCT Pub. Date: Sep. 18, 1980

[30] Foreign Application Priority Data

Mar. 16, 1979 [SE] Sweden ............................... 7902378

[51] Int. Cl.$^3$ ............................................ G01N 25/18
[52] U.S. Cl. ................................... 374/44; 364/557
[58] Field of Search ............... 73/15 R, 15 A, 190 H, 73/193 R; 364/557

[56] References Cited

U.S. PATENT DOCUMENTS

| | | | |
|---|---|---|---|
| 2,878,669 | 3/1959 | Knudson et al. | 73/15 |
| 3,229,499 | 1/1966 | Shayeson et al | 73/15 |
| 3,436,534 | 4/1969 | Wallace | 364/557 |
| 3,552,185 | 1/1971 | Goode et al. | 73/15 |
| 3,979,952 | 9/1976 | Bornstein | 73/193 |
| 4,236,403 | 12/1980 | Poppendiek | 73/15 |

FOREIGN PATENT DOCUMENTS

| | | |
|---|---|---|
| 2057174 | 5/1971 | France . |
| 49223 | 3/1919 | Sweden . |
| 442793 | 1/1968 | Switzerland . |

*Primary Examiner*—Herbert Goldstein
*Attorney, Agent, or Firm*—Cushman, Darby & Cushman

[57] ABSTRACT

The invention relates to a portable, battery-driven device for measuring heat transfer coefficients (k-values). It uses an amplifier (1), which forms the quotient between the inner temperature minus the inner wall temperature on one hand and the inner temperature minus the outer temperature on the other hand. The temperature values of the first-mentioned substraction are obtained by thermal elements (7, 8), which are connected to the device. The difference according to the second one of the substractions is adjustable connected in a feed back circuit of the amplifier (1). The output quantity of the latter is supplied to an instrument (3) graduated in k-value. The thermal element for the measuring of the inner wall temperature can be provided at the tip of a probe (9), and may consequently be conveniently applied to different places of a wall to be investigated.

9 Claims, 1 Drawing Figure

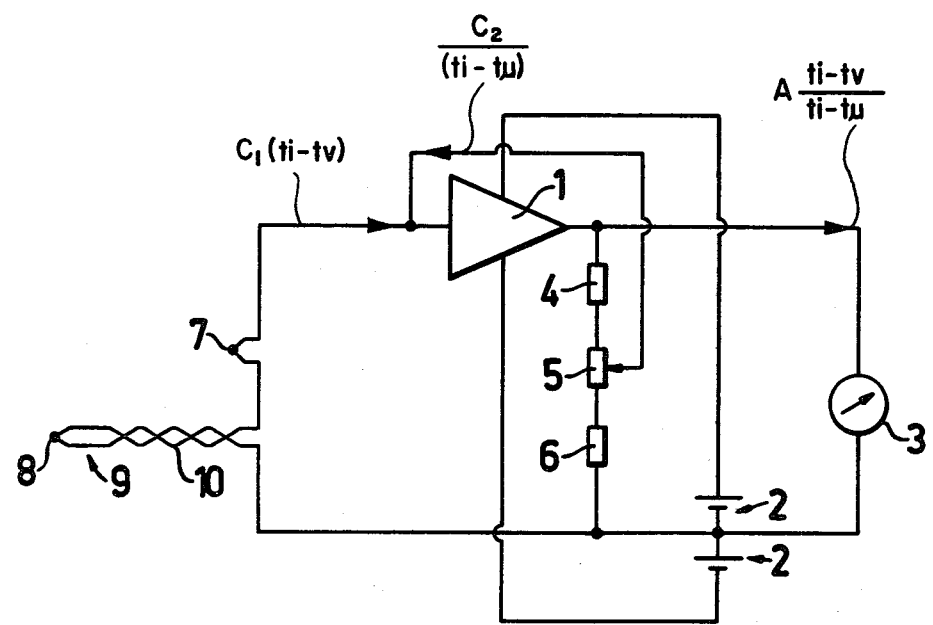

HEAT TRANSFER METER

The invention provides a meter for measuring a heat transmission coefficient of a structure such as a wall separating media having different temperatures.

BACKGROUND OF THE INVENTION

In recent years it has been more and more important to dimension the insulation of buildings in an economical manner. With increasing costs of heating it has been necessary to check and to improve such an insulation. For this purpose various techniques and arrangements for measuring heat transmission through walls have come into use. One such technique utilizes a heat camera to sense heat transfer through portions of a wall. Such techniques have been useful in establishing the existence of heat leakages in walls, which leakages one has not been earlier indentifiable. However, using that technique has the disadvantage that it requires a considerable amount of equipment and is relatively expensive.

It is therefore desirable to be able to measure heat transmission in a simple manner and to be able to survey the heat transmission in whole wall areas, windows or doors. For that purpose a meter for such a measuring task should be portable, simple to operate and it should rapidly give measuring results. The invention relates to a device for making this possible.

SUMMARY OF THE INVENTION

The present invention provides a meter for measuring a heat transmission coefficient of a wall separating media having different temperatures. The meter is highly portable, easy to operate and provides measured results rapidly. Specifically, it provides a device for measuring a heat transmission coefficient for a wall portion separating an inner media having a temperature $t_i$ and an outer median having a temperature $t_u$, comprising, an amplifier having an input and an output, an indicator coupled to said output for indicating the measured heat transfer coefficient, first thermal sensor means adapted for sensing a temperature tv of said wall portion at a surface thereof on its inner media side, a second thermal sensor means for sensing said temperature ti of said inner media, said first and second thermal sensors being connected in an input circuit coupled to said amplifier input to provide a signal proportional to $(t_i - t_v)$; and feedback circuit means coupled at least in part from said output to said input, said circuit being adjustable to provide a feedback signal to said input for causing the gain of said amplifier to be proportional to $1/(t_i - t_u)$, whereby there is developed at said output a signal proportional to $A(t_i - t_v)/(t_i - t_u)$ indicative of said heat transmission coefficient, where A is a constant selected for calibrating said indicator to a predetermined scale.

According to the invention an electronic amplifier is used which forms the quotient between two quantities. The first quantity is the inner temperature minus the inner wall temperature and the second quantity is the inner temperature minus the outer temperature, the temperature values of the first quantity being obtained by means of thermal elements, which are connected to the device, and the second quantity being settable by adjusting a feed-back circuit of the amplifier. An output of the amplifier is supplied to an indicator graduated in units of heat transfer coefficient k.

The invention thereby starts from the following relation between the heat transmission coefficient k and the temperature which influences the measuring:

$$k = A(t_i - t_v)/(t_i - t_u) \, W/m^2 \, °C.$$

where A is a quantity which includes the heat transfer coefficient for radiation and for convection as well as apparatus parameters and where $t_i$ is the inner temperature in a room where the measuring is performed, $t_v$ is the inner wall temperature in said room and $t_u$ is the outer temperature outside the wall inside which the measuring is made.

Equation (1) is derived from a combination of two basic formulas describing heat flow as follows:

$$P_t = k(t_i - t_u) W/m^2 \tag{2}$$

where
 $t_i$ = inner (room) temperature
 $t_u$ = outer temperature
 k = heat transmission coefficient $$P_t = (t_i - t_v)(3) \, W/m^2 \tag{3}$$

where $t_v$ = inner wall temperature
 = heat transfer coefficient (fairly constant for the particular medium, in this case air)

Equations (2) and (3) are combined to yield $$k = \alpha(t_i - t_v)/(t_i - t_u) \tag{4}$$

to obtain equation (1), α in equation (4) is replaced by A to take into account apparatus parameters transforming temperature differences into electrical units. The difference $t_i - t_u$ can be measured with conventional thermometers and the corresponding number of degrees can for instance be adjusted by manipulating a graduated knob of a potentiometer forming part of a feed back circuit controlling the gain of the amplifier. The feedback circuit sets the gain of the amplifier to a value proportional to $1/(t_i - t_u)$. The difference $t_i - t_v$ is obtained by means of thermal elements, which are connected to an input of the device.

BRIEF DESCRIPTION OF THE DRAWING

The single FIGURE is a circuit diagram embodying an example of the disclosed invention.

DETAILED DESCRIPTION OF THE INVENTION

The invention will be described more in detail in connection with the enclosed drawing, which shows an amplifier 1, such as example an operational amplifier, which is supplied with power from a current source 2 and the output of which is connected to an indicator 3. The amplifier has a feed-back circuit, here shown as a voltage divider with the resistors 4, 5 and 6, of which the resistor 5 is a potentiometer, from the tap of which the feed back quantity is derived. The potentiometer is manually adjusted by a graduated knob (not shown) to produce an amplifier gain inversely proportional to (eitu) which can be measured with conventional thermostats. The difference between the voltages from two thermal elements 7 and 8 which are oppositely paled and wired in series is supplied to an input on the amplifier. One thermal element, 7, is mounted in the housing of the device while the other thermal element, 8, is mounted in a probe tip, 9, which is connected by a conductor 10 to the input circuit of the amplifier. Through a suitable choice of the shown and implicit circuit elements of the devide, which latter need not be described in detail for the understanding of the mode of operation of the invention, the relation according to equation (1) can be realized with the required accuracy and the heat transmission coefficient k can be read directly on the indicator 3.

With the device one can measure the heat transmission coefficient k by aid of the probe and can survey the heat transmission in a wall, a door or a window.,

We claim:

1. A device for measuring a heat transmission coefficient for a wall portion separating an inner media having a temperature $t_i$ and an outer media having a temperature $t_u$, comprising:
   an amplifier having an input and an output;
   an indicator coupled to said output for indicating the measured heat transfer coefficient;
   first thermal sensor means adapted for sensing a temperature $t_v$ of said wall portion at a surface thereof on its inner media side;
   second thermal sensor means for sensing said temperature $t_i$ of said inner media, said first and second thermal sensors being connected by an input circuit coupled to said amplifier input to provide a signal proportional to $(t_i - t_v)$; and
   feedback circuit means coupled at least in part from said output to said input, said circuit being adjustable to provide a feedback signal to said input for causing the gain of said amplifier to be proportional to $1/(t_i - t_u)$, whereby there is developed at said output a signal proportional to $A(t_i - t_v)/(t_i - t_u)$ indicative of said heat transmission coefficient, where A is a constant selected for calibrating said indicator to a predetermined scale.

2. A device according to claim 1 further including
   a housing in which is mounted said amplifier, indicator, second thermal sensor and feedback circuit; and
   a probe, coupled to said housing, for containing said first thermal sensor so positioned that it can be brought into contact with said wall portion surface.

3. A device according to claim 1 or 2 wherein said feedback circuit comprises a manually adjustable potentiometer having positional settings corresponding to the temperature difference between inner and outer media $(t_i - t_u)$.

4. A device according to claim 1 or 2 wherein said input circuit comprises a series connection of said first and second thermal sensors.

5. A device according to claim 3 wherein said input circuit comprises a series connection of said first and second thermal sensors.

6. A device according to claim 1 or 2 wherein said amplifier is an operational amplifier.

7. A device according to claim 3 wherein said amplifier is an operational amplifier.

8. A device according to claim 4 wherein said amplifier is an operational amplifier.

9. A device according to claim 5 wherein said amplifier is an operational amplifier.

* * * * *